United States Patent [19]

Nestler et al.

[11] Patent Number: 5,254,527
[45] Date of Patent: Oct. 19, 1993

[54] OPTICALLY ACTIVE HERBICIDAL ETHYL-2-(4-(6-CHLORO-BENZOXAZOL-2-YLOXY)-PHENOXY)-PROPIONATE

[75] Inventors: Hans J. Nestler, Königstein/Taunus; Gerhard Hörlein, Frankfurt am Main; Reinhard Handte, Hofheim am Taunus; Hermann Bieringer, Eppstein/Taunus; Friedhelm Schwerdtle, Frankfurt am Main; Peter Langelüddeke, Hofheim am Taunus; Peter Frisch, Frankfurt am Main, all of Fed. Rep. of Germany

[73] Assignee: Hoechst Aktiengesellschaft, Frankfurt am Main, Fed. Rep. of Germany

[21] Appl. No.: 790,128

[22] Filed: Nov. 7, 1991

Related U.S. Application Data

[60] Continuation of Ser. No. 663,274, Feb. 28, 1991, abandoned, which is a continuation of Ser. No. 434,490, Nov. 9, 1989, abandoned, which is a continuation of Ser. No. 144,612, Jan. 11, 1988, abandoned, which is a continuation of Ser. No. 730,295, May 3, 1985, abandoned, which is a division of Ser. No. 971,427, Dec. 20, 1978, Pat. No. 4,531,969.

[30] Foreign Application Priority Data

Dec. 24, 1977 [DE] Fed. Rep. of Germany ....... 2758002

[51] Int. Cl.$^5$ .................... A01N 43/76; C07D 263/58
[52] U.S. Cl. .................................... 504/270; 548/221
[58] Field of Search ............................ 71/88; 504/270; 548/221

[56] References Cited

U.S. PATENT DOCUMENTS

| | | | |
|---|---|---|---|
| 4,130,413 | 12/1978 | Handte et al. | 71/88 |
| 4,175,947 | 11/1979 | Koch et al. | 71/108 |
| 4,270,948 | 6/1981 | Takahashi et al. | 71/108 |

OTHER PUBLICATIONS

Morrison and Boyd, "Organic Chemistry", 3rd Ed. pp.123–131, 135–137 and 235–237 (Allyn and Bacon), 1973.
"Pesticide manual" 9th edition, 1991, pp. 484 and 828.

Primary Examiner—Richard L. Raymond
Assistant Examiner—B. Bembenick
Attorney, Agent, or Firm—Curtis, Morris & Safford

[57] ABSTRACT

Optically active enantiomers of the formula I

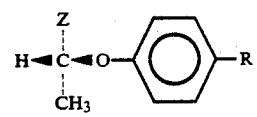

where R is a group of the formulae

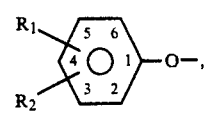

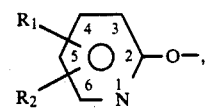

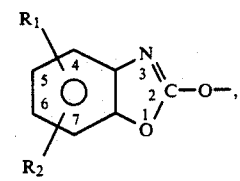

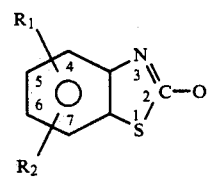

or
(Abstract continued on next page.)

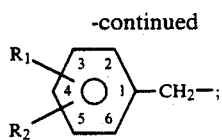
$R_1$ and $R_2$, among others, are halogen or $CF_3$ and Z is a carboxyl, carboxylate, carboxylic acid ester, thioester, carbonamide, carboxylic acid anilide, carbohydrazide or thioamide group, are interesting herbicides the effect of which is considerably superior to that of the optically inactive racemates.
12 Claims, No Drawings

OPTICALLY ACTIVE HERBICIDAL ETHYL-2-(4-(6-CHLORO-BENZOXAZOL-2-YLOXY)-PHENOXY)-PROPIONATE

This application is a continuation of application Ser. No. 07/663,274, filed Feb. 28, 1991, now abandoned which is a continuation of application Ser. No. 07/434,490, filed Nov. 9, 1989, now abandoned, which in turn is a continuation of application Ser. No. 07/144,612, filed Jan. 11, 1988, now abandoned, which in turn is a continuation of application Ser. No. 06/730,295, filed May 3, 1985, now abandoned, which in turn is a division of application Ser. No. 05/971,427, filed Dec. 20, 1978, now U.S. Pat. No. 4,531,969, issued Jul. 30, 1985.

It is known that many biologically effective natural products are optically active because of the presence of one or more asymmetric carbon atoms, that is, they turn the plane of polarized light to the right (+) or to the left (−). Often, these compounds have a better biological effect than corresponding synthetic, optically inactive compounds. Synthetically prepared active substances such as pharmaceuticals or plant protecting agents having asymmetric carbon atoms which are generally obtained in the form of optically inactive racemates, that is, mixtures of equal amounts of dextrorotatory and levorotatory enantiomers, sometimes behave in a similar manner. In these cases, too, it is often observed after isomer separation that one of the two enantiomers has an increased activity as compared with the racemate. However, it cannot be predicted whether the levorotatory (−) or the dextrorotatory (+) form is the more active one, and whether there is any relation between effectiveness and optical activity.

Compounds of the class of p-substituted alpha-phenoxypropionic acid derivatives are of interest because of their specific herbicidal action against weed grasses (see for example U.S. Pat. Nos. 3,954,442; 4,088,474; and 4,175,947, as well as German Offenlegungsschriften Nos. 24 33 067; 25 31 643; 26 23 558; 25 46 251; and 26 01 548). These compounds have an asymmetric carbon atom adjacent to the carbonyl function, so that at least two enantiomeric, optically active forms exist which are generally defined as D and L form.

It has now been found that the D-enantiomers of these compounds are distinguished by a considerably increased herbicidal action as compared with the racemates.

Subject of the present invention are therefore D-(alpha-phenoxy)-propionic acid derivatives of the formula I

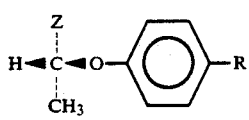

where
R is a group of the formulae

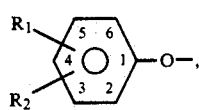

-continued

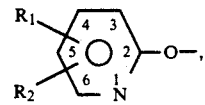

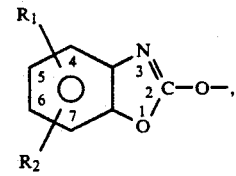

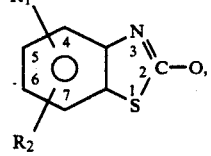

or

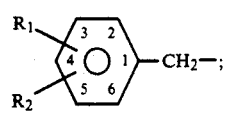

in which
$R_1$ is hydrogen, halogen or $CF_3$; $R_2$ is hydrogen, $C_1$–$C_4$-alkyl, halogen or $NO_2$;
with the proviso that when R is a radical of the formulae II, III or VI, $R_1$ is other than hydrogen;
Z is a group of the formulae

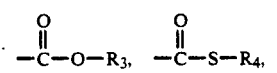

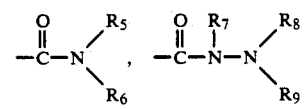

or

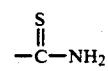

in which
$R_3$ is H ($C_1$–$C_{12}$)-alkyl, optionally substituted by 1-6 halogen atoms and/or OH, ($C_1$–$C_6$)-alkoxy, ($C_1$–$C_4$)-alkylthio, ($C_1$–$C_6$)-alkoxy-($C_2$–$C_6$)-alkoxy, halo-($C_1$–$C_2$)-alkoxy, methoxy-ethoxy-ethoxy, ($C_1$–$C_4$)-alkylamino, D-($C_1$–$C_4$)-alkylamino, phenyl, oxiranyl or phenoxy, the latter one optionally being mono- or disubstituted by halogen and/or ($C_1$–$C_4$)-alkyl; ($C_5$–$C_6$)-cycloalkyl or halo-($C_5$–$C_6$)-cycloalkyl; ($C_3$–$C_6$)-alkenyl, halogeno-($C_3$–$C_6$)-alkenyl or ($C_5$–$C_6$)-cycloalkenyl; ($C_3$–$C_4$)-alkinyl, optionally mono- or disubstituted by ($C_1$–$C_6$)-alkyl, phenyl, halogen or ($C_1$–$C_2$)-alkoxy; phenyl, optionally mono- to trisubstituted by ($C_1$–$C_4$)-alkyl, ($C_1$–$C_4$)-alkoxy, halogen, $NO_2$ or $CF_3$; furfuryl, tetrahydrofurfuryl or a cation equivalent of an oragnic or inorganic base;
$R_4$ is ($C_1$–$C_6$)-alkyl optionally substituted by ($C_1$–$C_4$)-alkoxy, halogen or phenyl, the latter one optionally being mono- to trisubstituted by $(C_1-C_4)$-alkyl or halogen; $(C_3-C_6)$-alkenyl or phenyl optionally mono- to trisubstituted by $(C_1-C_4)$-alkyl and/or halogen;

$R_5$ and $R_6$, being identical or different, each are H, $(C_1-C_6)$-alkyl, hydroxy-$(C_1-C_6)$-alkyl, $(C_5-C_6)$-cycloalkyl or phenyl optionally mono- to trisubstituted by $(C_1-C_4)$-alkyl, $(C_1-C_4)$-alkoxy, halogen or $CF_3$ (with the proviso that not both $R_5$ and $R_6$ are phenyl), or together form a methylene chain having 2, 4 or 5 members, wherein a $CH_2$ group may be substituted by 0, NH or $N(CH_3)$;

$R_7$ is H or $CH_3$;
$R_8$ is H, $CH_3$, or $C_2H_5$;
$R_9$ is H, $CH_3$, $C_2H_5$ or phenyl;

with the proviso that when $R_1$ is trifluoromethyl, $R_2$ is hydrogen and R is a group of formula II, $R_3$ is other than hydrogen.

In this specification, halogen always means chlorine or bromine.

The above compounds are obtained by reacting
a) correspondingly substituted phenols or phenolates of the formula

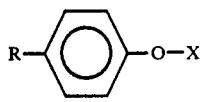

(VII)

where X is an alkali metal or hydrogen atom, with substituted L-propionic acid esters of the formula

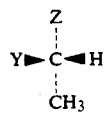

(VIII)

where Y is chlorine, bromine or a sulfonyloxy group; or b) when R is a radical of formula III, IV or V, also by reacting compounds of the formula

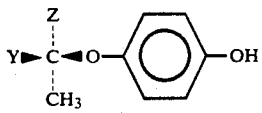

(IX)

with correspondingly substituted 2-halo-pyridines, halo-benzothiazoles or halo-benzoxazoles;
and, if desired, converting the compounds of the formula I obtained into other compounds of formula I by methods generally known.

In the process of the invention according to a) a Walden inversion occurs, whereby the L-configuration of the propionic acid derivative is converted to the D-configuration of the final product.

a) Process variant a) is carried out according to generally known operation methods. When a phenol is used as starting material (X = H), the reaction is preferably carried out in the presence of an alkali metal carbonate as acid-binding agent, and in a polar solvent, preferably acetone, methylethylketone, acetonitrile, dimethyl formamide or dimethyl sulfoxide, at temperatures of from 50° to 150° C. When a phenolate is used as starting compound of formula VII (X=alkali metal atom, preferably Na or K), the use of high-boiling solvents such as toluene, xylene, DMF or DMSO is recommended, at temperatures of from 100° to 150° C. By the sulfonyloxy group in Y, there is to be understood the $R_{10}-SO_2O-$ group, where $R_{10}$ is an aliphatic or aromatic radical, preferably the mesylate radical ($CH_3SO_2O-$), the ($CF_3SO_2O-$)radical, the benzenesulfonate radical, the tosylate radical (p-$CH_3-C_6H_4-SO_2O-$) or a benzenesulfonate radical substituted by $NO_2$ or $OCH_3$.

b) The reaction according to b) proceeds under similar conditions as that of a). The starting compounds of formula IX are obtained from hydroquinone-monobenzyl ether or its alkali metal salts of the formula

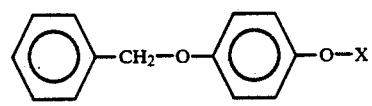

(X)

by reaction with compounds of the formula VIII and hydrogenolytic splitting-off of the benzyl group. Suitable catalysts are noble metal catalysts such as palladium/charcoal.

If desired, the compounds of formula I obtained according to a) or b) may be converted into other compounds of formula I according to processes generally known. For example, salts ($R_3=$cat) are obtained from esters by alkaline saponification and may be converted into the free acids ($R_3=$H). These in turn, via their halides, yield the corresponding amides, hydrazides or thioesters. Esterification of the free acids or the acid chlorides, or direct ester interchange yields other esters of formula I.

When optically pure starting material is used, the processes of the invention give final products having an optical purity of at, least 60% corresponding to an 80% amount of D form. If desired, the optical purity of the compounds can be further increased according to known methods, for example recrystallization. In the case where these compounds, especially the esters, are liquid, purification is preferably carried out by saponifying the ester obtained in the first place to form the corresponding phenoxypropionic acid, freeing this from residual amounts of L form by recrystallization and subsequently preparing the intended compound of formula I from the substantially pure acid according to one of the aforementioned process variants.

Preferred compounds of formula I are those where the $R_1/R_2$ pair represents H/Cl, H/Br, H/$CF_3$, CL/$CF_3$, Cl/Cl, Cl/Br, or, if R is a radical of the formulae IV or V, also H/H. When R is a radical of the formulae II or III, the radicals $R_1$ and $R_2$ are preferably in 4- or in 2,4-position, while in the case where R is a radical of the formulae IV or V, the 5- and 6-positions are especially preferred.

By way of example, the following compounds shall be mentioned as having good activity:

D-2-/-4-(4-chlorophenoxy)-phenoxy-7-propionic acid,
D-2-/-4-(4-chlorophenoxy)-phenoxy-7-propionic acid-methyl ester, -n-propylester, -isopropylester,
D-2-/-4-(2,4-dichlorophenoxy)-phenoxy-7-propionic acid, sodium-D-2-/-4-(2,4-dichlorophenoxy)phenoxy-7-propionate,
dimethylammonium-D-2-/-4-(2,4-dichlorophenoxy)-phenoxy-7-propionate,
D-2-/-4-(2,4-dichlorophenoxy)-phenoxy-7-propionic acid-isopropyl ester, -isobutyl ester, -n-amyl ester, D-2-/.
  -4-(4-bromo-2-chlorophenoxy)-phenoxy-7-propionic acid-n-propyl ester, potassium-D-2-/.
  -4-(4-bromo-2-chlorophenoxy)-phenoxy-7-propionate,
diethylammonium-D-2-/.
  -4-(4-bromo-2-chlorophenoxy)-phenoxy-7-propionate,
D-2-/.4-(4-bromo-2-chlorophenoxy)-phenoxy-7-propionic acid-sec.-amyl ester,
ammonium-D-2-/.
  -4-(4-trifluoromethylphenoxy)-phenoxy-7-propionate,
methylammonium-D-2-/.
  -4-(4-trifluoromethylphenoxy)phenoxy-7-propionate,
D-2-/.
  -4-(4-trifluoromethylphenoxy)-phenoxy-7-propionic acid-n-propyl ester, -isobutyl ester,
D-2-/.
  -4-(2-chloro-4-trifluoromethyl-phenoxy)-phenoxy-7-propionic acid, -methyl ester, -ethyl ester, n- and i-propyl ester, n- and i-butyl ester, -Na- and K-salt,
D-2-/.-4-(4-chlorobenzyl)-phenoxy-7-propionic acid,
D-2-/.-4-(2,4-dichlorobenzyl)-phenoxy-7-propionic acid-methyl ester, -ethyl ester, -isobutyl ester,
D-2-/.-4-(2,4-dichlorobenzyl)-phenoxy-7-propionic acid-propyl ester, -isoamyl ester, -ethyl ester,
D-2-/.-4-(2,4-dichlorobenzyl)-phenoxy-7-propionic acid, sodium-D-2-/.
  -4-(2,4-dichlorobenzyl)-phenoxy-7-propionate,
D-2-/.
  -4-(3,5-dichloro-2-pyridyloxy)-phenoxy-7-propionic acid,
D-2-/.
  -4-(3,5-dichloro-2-pyridyloxy)-phenoxy-7-propionic acid-methyl ester, -ethyl ester, -propyl ester, -isopropyl ester, -isobutyl ester, -sodium salt,
D-2-/.
  -4-(5-chloro-2-benzoxazolyloxy)-phenoxy-7-propionic acid-methyl ester, -ethyl ester, -propyl ester, -isopropyl ester, -isobutyl ester,
D-2-/.
  -4-(6-chloro-2-benzoxazolyloxy)-phenoxy-7-propionic acid-methyl ester, -ethyl ester, -propyl ester, -isopropyl ester, -isobutyl ester,
D-2-/.
  -4-(6-chloro-2-benzothiazolyloxy)-phenoxy-7-propionic acid-methyl ester, -ethyl ester, -propyl ester, -isopropyl ester, -isobutyl ester,
D-2-/.-4-(2-benzothiazolyloxy)-phenoxy-7-propionic acid-methyl ester, -ethyl ester,
D-2-/.-4-(2-benzoxazolyloxy)-phenoxy-7-propionic acid-methyl ester, -ethyl ester,
D-2-/.
  -4-(6-bromo-2-benzothiazolyloxy)-phenoxy-7-propionic acid-ethyl ester,
D-2-/.
  -4-(6-bromo-2-benzoxazolyloxy)-phenoxy-7-propionic acid-ethyl ester.
The following compounds may also be mentioned:
D-2-/.-4-(4-chlorophenoxy)phenoxy-7-propionic acid-2-chloroethyl ester, -2,3-dichloro-n-propyl ester, -cyclohexyl ester, -propargyl ester, ethylthiol ester, -dimethylamide,
D-2-/.-4-(2,4-dichlorophenoxy)-phenoxy-7-propionic acid -2-methylaminoethyl ester, -allyl ester, -3,4-dichlorobenzyl ester, -diethylamide, -$^2$N-methylhydrazide, -thioamide, D-2-/ -(4-broino-2-chlorophenoxy)-phenoxy-7-propionic acid-2-ethylthioethyl ester, -N-n-propylaminoethyl ester, -2-chloro-allyl ester, -4-chlorobenzylthiol ester, -phenyl-hydrazide,
D-2-/.
  -4-(4-trifluoromethyl-phenoxy)-phenoxy-7-propionic acid-2-(4-chlorophenyl)-ethyl ester, -n-octyl ester, -methylallyl ester, -(3-phetiyl)-propargyl ester, -n-propylamide,
D-2-/.-4-(2,4-dichlorobenzyl)-phenoxy-7-propionic acid-n-dodecyl ester, -benzylthio ester, -cyclohexylamide, -$^1$N,$^2$N-dimethylhydrazide,
D-2-/.-4-(4-chlorobenzyl)-phenoxy-7-propionic acid-cyclopentyl ester, -ethoxyethylamide,
D-2-/.
  -4-(2-chloro-4-trifluoromethylphenoxy)-phenoxy-7-propionic acid-ethyl ester, -2-methoxyethyl ester, -n-hexyl ester, -cyclohexyl ester, -amide -anilide, -p-chloroanilide,
D-2-/.-4-(5-chloro-2-pyridyloxy)-phenoxy-7-propionic acid,
D-2-/.-4-(5-chloro-2-pyridyloxy)-phenoxy-7-propionic acid-methyl ester, -isoamyl ester, -methoxyethyl ester, -3-methoxybutyl ester, -2-chloropropyl ester, -allyl ester, -propargyl ester,
D-2-/.-4-(5-bromo-2-pyridyloxy)-phenoxy-7-propionic acid,
D-2-/.-4-(5-bromo-2-pyridyloxy)-phenoxy-7-propionic acid-methyl ester, -ethyl ester, -amide, -dimethylamide, -hydrazide, -anilide,
D-2-/.
  -4-(3,5-dichloro-2-pyridyloxy)-phenoxy-7-propionic acid-isobutyl ester, -2-chlorethyl ester, -1-methylpropargyl ester, -cyclohexyl ester, -cyclohexenyl ester, -2-chlorocyclohexyl ester, -butoxyethyl ester, -methoxyethyl ester, -6-chlorohexyl ester, -amide, -dimethylamide, -dimethylamide, -anilide, -potassium salt, -ammonium salt, -dimethylammonium salt,
D-2-/.
  -4-(3-chloro-5-bromo-2-pyridyloxy)-phenoxy-7-propionic acid,
D-2-/.
  -4-(3-chloro-5-bromo-2-pyridyloxy)-phenoxy-7-propionic acid-methyl ester, -ethyl ester,
D-2-/.
  -4-(3-bromo-5-chloro-2-pyridyloxy)-phenoxy-7-propionic acid-isopropyl ester,
D-2-/.
  -4-(5-chloro-3-methyl-2-pyridyloxy)-phenoxy-7-propionic acid,
D-2-/.
  -4-(5-chloro-3-methyl-2-pyridyloxy)-phenoxy-7-propionic acid-methyl ester, -ethyl ester,
D-2-/.-4-(2-benzothiazolyloxy)-phenoxy-7-propionic acid-isobutyl ester, -3-chloropropyl ester, -allyl ester, -1-phenylpropargyl ester, -amide,
D-2-/.
  -4-(5-chloro-2-benzothiazolyloxy)-phenoxy-7-propionic acid-methyl ester, -ethyl ester, -isobutyl ester,
D-2-/.
  -4-(6-chloro-2-benzothiazolyloxy)-phenoxy-7-propionic acid-isoamyl ester, -isooctyl ester, -2-chloroethyl ester, -3-chloropropyl ester, -1,2-dichloroisopropyl ester, -6-chlorohexyl ester, -2-methoxyethyl ester, -2-butoxyethyl ester, -3-methoxybutyl ester, -allyl ester, -cyclohexyl ester, -1,1-dimethylpropargyl ester, -cyclohexenyl ester, D-2-/-
-4-(6-trifluoromethyl-2-benzolhiazolyloxy)-phenoxy-
7-propionic acid-methyl ester, -ethyl ester, -propyl
ester, isopropyl ester, -isobutyl ester, D-2-/-
-4-(5-trifluoromethyl-2-benzolhiazolyloxy)-phenoxy-
7-propionic acid-methyl ester, -ethyl ester, D-2-/-
-4-(6-bromo-2-benzothiazolyloxy)-phenoxy-7-propionic acid-methyl ester, -propyl ester, -isobutyl ester, D-2-/-
-4-(5-bromo-2-benzothiazolyloxy)-phenoxy-7-propionic acid-ethyl ester, D-2-/-
-4-(5-bromo-2-benzoxazolyloxy)-phenoxy-7-propionic acid-methyl ester, -ethyl ester, -isopropyl ester, -isobutyl ester, D-2-/-
-4-(6-bromo-2-benzoxazolyloxy)-phenoxy-7-propionic acid-methyl ester, -propyl ester, -isobutyl ester, D-2-/-
-4-(6-trifluoromethyl-2-benzoxazolyloxy)-phenoxy-7-propionic acid-methyl ester, -ethyl ester, -propyl ester, D-2-/-
-4-(5-chloro-2-benzoxazolyloxy)-phenoxy7-propionic acid-isoamyl ester, -2-chloroethyl ester, -3-chloropropyl ester, -2-methoxyethyl ester, -3-methoxybutyl ester, -methoxyethoxyethyl ester, -cyclohexyl ester, -allyl ester, -propargyl ester, D-2-/-
-4-(6-chloro-2-benzoxazolyloxy)-phenoxy-7-propionic acid-isobutyl ester, -1,2-dichloroisopropyl ester, -6-chlorohexyl ester, -1-methoxyethyl ester, -cyclohexyl ester, -2-chlorocyclohexyl ester, -i-ethylpropargyl ester.

As already mentioned, the D-enantiomers of the invention are distinguished by a considerably increased herbicidal action as compared to that of the racemates. Surprisingly, it has been observed that the L-enantiomers are practically ineffective in the post-emergence process, so that the efficiency of the racemates is practically due to their content of D-enantiomers.

This invention therefore also comprises herbicides containing an active compound of formula I, which contains less than 20, preferably less than 10, especially less than 5, weight % of L-enantiomer, in combination with usual auxiliaries and carriers. Formulations for practical application are made according to the same methods as already known for the racemates, using the same additives. Preferred are liquid formulations or ULV formulations, which contain from 2 to 95% of the active substance, depending on the kind of formulation. Because of the increased efficiency, the required application concentration of the optically active substances of the invention per unit of area can be reduced by up to 50% as compared to the racemates; generally, it is from 0.01 to 5 kg/ha, preferably from 0.05 to 3 kg/ha.

The following Examples illustrate the invention.

EXAMPLES OF FORMULATION

Example 1

D-(+)-2-/-4-(4-chlorophenoxy)-phenoxy-7-propionic acid-ethyl ester

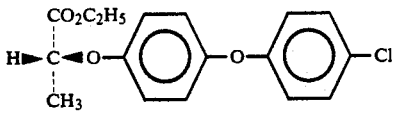

220.5 g (1.0 mol) 4-(4-chlorophenoxy)-phenol are refluxed for 56 hours with 299.2 g (1.1 mols) L-(—)-lactic acid ethyl ester tosylate and 158.7 g (1.15 mols) pulverized anhydrous potassium carbonate in 1000 ml methyl ethyl ketone. After cooling the product is filtered off from the salt residue, the solvent is evaporated and the remaining residue is disfilled under highly reduced pressure. 310 (97% of th.) D-(+)-2-/-
-4-(4-chlorophenoxy)-phenoxy-7-propionic acid ethyl ester, b.p. 159° C./0.04 mm, $\alpha_D^{20} = 6.50°$ (1 m, chloroform) are obtained.

Example 2

D-(+)-2-/-4-(4-chlorophenoxy)-phenoxy-7-propionic acid

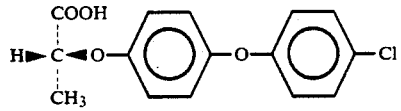

32.1 g (0.10 mol) D-(+)-2-/-4-(4-chlorophenoxy)-phenoxy-7-propionic acid ethyl ester are dissolved in 150 cc of methanol, and 125 cc of 2N-sodium hydroxide solution (0.25 mol) are added with agitation. The batch is heated to reflux temperature for 2 hours, subsequently the substantial part of the organic solvent is distilled off, and, after cooling, the product; is precipitated by adding hydrochloric acid. After suction-filtration, washing with water and drying, 28.5 g (97% of th.) D-(+)-2-/-
-4-(4-chlorophenoxy)-phenoxy-7-propionic acid, m.p. 105°-110° C., $\alpha_D^{20} = 1.6°$ (0.4 mm, chloroform) are obtained.

Example 3

D-(+)-2-/-4-(4-chlorophenoxy)-phenoxy-7-propionic acid -isobutyl ester

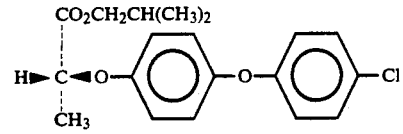

A. By Ester Interchange 160.3 g (0.5 mol) of D-(+)-2-/-4-(4-chlorophenoxy)-phenoxy-7-propionic acid ethyl ester are dissolved in 500 cc of isobutyl alcohol. After adding 2 cc of concentrated sulfuric acid, the batch is refluxed for 8 hours while distilling off the ethanol which has formed via a column. Subsequently, the substantial part of the solvent is distilled off in vacuo, the residue is dissolved in methylene chloride and washed with water. After distilling off the methylene chloride the product is distilled under highly reduced pressure. 159.0 g (91% of th.) D-(+)-2-/.-4-(4-chlorophenoxy) -phenoxy.7-propionic acid-isobutyl ester, b.p. 169°–173° C./0.05 mm, $\alpha_D^{20}=7.4°$ (1 m, chloroform) are obtained.

B. By Esterification 29.3 g (0.1 mol) of D-(+)-2-/.-4-(4-chlorophenoxy) -phenoxy.7-propionic acid are dissolved in 200 cc of isobutyl alcohol. After addition of 0.5 cc of concentrated sulfuric acid, the batch is refluxed for 15 hours, while distilling off the water which has formed via a column. Subsequently, the substantial part, of the solvent is distilled off in a water jet vacuum, the residue is dissolved in methylene chloride and washed with water. After evaporation of the methylene chloride the product is distilled under highly reduced pressure. 30.1 g (86% of th.) D-(+)-2-/.-4-(4-chlorophenoxy) -phenoxy.7-propionic acid isobutyl ester, b.p. 167° C./0.04 mm, $\alpha_D^{20}=7.50°$ (1 m, chloroform) are obtained.

Example 4

D-(+)-2-/.. -4-(2,4-dichlorophenoxy)-phenoxy.7-propionic acid methyl ester

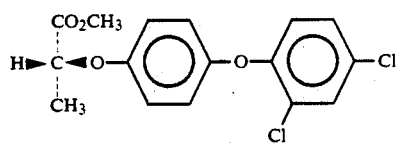

25.5 g (0.10 mol) of 4-(2,4-dichlorophenoxy)-phenol are refluxed for 14 hours together with 25.8 g (0.10 mol) of L-(−)-lactic acid methyl ester,.tosylate -and 15.2 g (0.11 mol) of pulverized, anhydrous potassium carbonate in 150 ml acetonitrile. After cooling, the product is filtered off from the salt residue, the solvent-is evaporated and the remaining residue is distilled under highly reduced pressure.

28.1 g (82% of th.) of D-(+)-2-/.-4-(2,4-dichloro -phenoxy)-phenoxy.7-propionic acid methyl ester, b.p. 167° C./0.03 mm, $\alpha_D^{20}=6.90°$ (1 m, chloroform) are obtained.

Example 5

D-(+)-2-/.. -4-(2,4-dichloro-phenoxy)-phenoxy.7-propionic acid ethyl ester

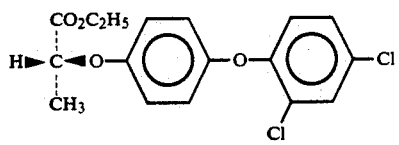

A. 27.7 g (0.10 mol) of dry sodium 4-(2,4-dichloro-phenoxy)-phenolate are suspended in 200 ml xylene and the suspension is heated to 110° C. within ½ hour, 20.6 g (0.105 mol) of L-(−)-lactic acid ethyl ester mesylate are added dropwise and the batch is refluxed for 4 hours.

After cooling the product, is separated from the precipitated salt residue, the solvent is evaporated and the remaining residue is distilled under highly reduced pressure.

17.0 g (48% of th.) D-(+)-2-/.. -4-(2,4-dichloro-phenoxy)-phenoxy.7-propionic acid ethyl ester, b.p. 196° C./0.05 mm, $\alpha_D^{20}=6.50°$ (1 m, chloroform) are obtained.

B. 10.2 g (0.040 mol) of 4-(2,4-dichlorophenoxy)-phenol are refluxed for 80 hours with 12.7 g (0.044 mol) L-(−)-lactic acid ethyl ester-4-methoxy-benzenesulfonate and 6.6 g (0.048 mol) of pulverized anhydrous potassium carbonate in 70 cc of acetone. After cooling the product is filtered off from the salt residue, the solvent is evaporated and the remaining residue distilled under highly reduced pressure.

11.5 g (81% of th.) D-(+)-2-/.. -4-(2,4-dichloro-phenoxy)-phenoxy.7-propionic acid ethyl ester, b.p. 180° C./0.03 mm, $\alpha_D^{20}=6.60°$ (1 m, chloroform) are obtained.

C. 3.0 g (11.6 mmols) of 4-(2,4-dichlorophenoxy)-phenol are refluxed for 24 hours with 3.5 g (11.6 mmols) of L-(−)-lactic acid ethyl ester-4-nitrobenzenesulfonate and 1.8 g (12.7 mmols) of pulverized anhydrous potassium carbonate in 40 cc of acetone. After cooling, the product is filtered off from the salt residue, the solvent and the remaining residue are distilled under highly reduced pressure.

3.6 g (87% of th.) D-(+)-2-/.. -4-(2,4-dichlorophenoxy) -phenoxy.7-propionic acid ethyl ester, b.p. 197° C./0.05 mm, $\alpha_D^{20}=4.7°$ (0.7 m, chloroform) are obtained.

Example 6A

D-(+)-2-/.. -4-(2,4-dichlorophenoxy)-phenoxy.7-propionic acid chloride

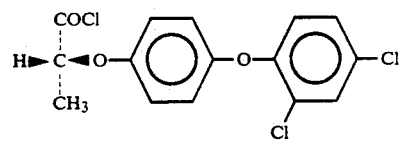

52.3 g (0.160 mol) of D-(+)-2-/.. -4-(2,4-dichlorophenoxy)-phenoxy.7-propionic acid, obtained by saponification according to Example 2 of the ethyl ester prepared according to Example 5, are dissolved in 200 cc of toluene. After addition of 22.8 g (0.192 mol) of thionyl chloride, the batch is refluxed for 13 hours.

By distillation under reduced pressure, the solvent and unreacted thionyl chloride are distilled off. The 61.3 g residue is dissolved in 238.7 g of benzene. Thus, an about 18% solution of D-(+)-2-/.. -4-(2,4-dichlorophenoxy)-phenoxy.7-proptonic acid chloride is obtained which can be used directly for further reactions.

Example 6B

D-(+)-2-/..-4-(2,4-dichlorophenoxy)-phenoxy.7-proptonic acid-2-(methoxy)-ethyl ester

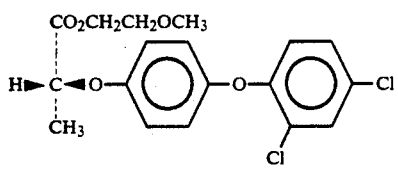

85 g of the benzenoic solution of D-(+)-2-/..-4-(2,4-dichlorophenoxy)-phenoxy.7-propionic acid chloride obtained in Example 6 A (about 45 mmols) are added dropwise at room temperature to a mixture of 3.8 g (50 mmols) of ethyleneglycol-monomethyl ether, 5.1 g (50 mmols) of triethylamine and 50 cc of benzene. Agitation is continued for a further 3 hours at 50° C. The batch is then cooled and filtered off from the precipitated triethylammonium hydrochloride. The filtrate is washed with water, the benzene is evaporated and the residue purified by chromatography on silica gel.

15.7 g (91% of th.) D-(+)-2-/..-4-(2,4-dichloro-phenoxy)-phenoxy.7-propionic acid-2-(methoxy)-ethyl ester, $\alpha_D^{20}=2.6°$ (0.5 m, chloroform) are obtained.

Example 7

D-(+)-2-/..-4-(2,4-dichlorophenoxy)-phenoxy.7-propionic acid-3-(methoxy)-n-butyl ester

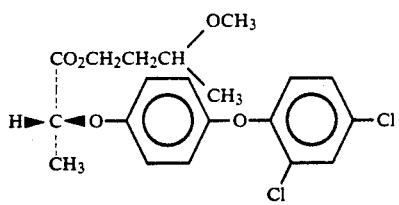

85 g of the benzenic solution of D-(+)-2-/..-4-(2,4-dichlorophenoxy)-phenoxy.7-propionic acid-chloride obtained in Example 6 A (about 45 mmols) are added dropwise at room temperature to a mixture of 5.2 g (50 mmols) of 3-methoxy-1-butanol, 5.1 g (50 mmols) of triethylamine and 50 cc of benzene. Agitation is continued for 3 hours at 50° C., the batch is cooled and filtered off from the precipitated triethylammonium hydrochloride. The filtrate is washed with water, the benzene is evaporated and the residue purified by chromatography on silica gel. 14.5 g (78% of th.) D-(+)-2-/.-4-(2,4-dichloro-phenoxy) -phenoxy.7-propionic acid-3-(methoxy)-n-butyl ester, $\alpha_D^{20}=3.0°$ (0.5 m, chloroform) are obtained.

Example 8

D-(+)-2-/..-4-(2,4-dichlorophenoxy)-phenoxy.7-propionic acid-tetrahydrofurfuryl ester

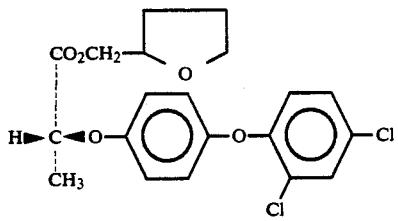

85 g of the benzenic acid solution of D-(+)-2-/..-4-(2,4-dichlorophenoxy)-phenoxy.7-propionic acid chloride obtained in Example 6 A (about 45 mmols) are added dropwise at room temperature to a mixture of 5.1 g (50 mmols) of tetrahydrofurfuryl alcohol, 5.1 g (50 mmols) of triethylamine and 60 cc of benzene. Agitation is continued for 3 hours at, 50° C. The batch is then cooled and filtered off from the precipitated triethylammonium hydrochloride. The filtrate is washed with water, the benzene is evaporated and the residue purified by chromatography on silica gel. 16.2 g (88% of th.) D-(+)-2-/.-4-(2,4-dichloro-phenoxy) -phenoxy.7-propionic acid-tetrahydrofurfuryl ester, $\alpha_D^{20}2.7°$ (0.5 m, chloroform) are obtained.

Example 9

D-(+)-2-/..-4-(4-bromo-2-chloro-phenoxy)-phenoxy.7-propionic acid ethyl ester

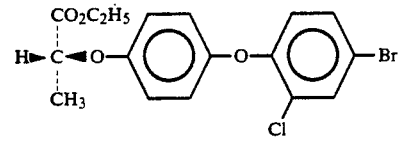

15.0 g (0.050 mol) of 4-(4-bromo-2-chlorophenoxy)-phenol are refluxed for 20 hours together with 10.2 g (0.052 mol) of L-(−)-lactic acid ethyl ester mesylate and 7.6 g (0.055 mol) of pulverized, anhydrous potassium carbonate in 100 cc of acetonitrile. After cooling the product is filtered off from the precipitated salt residue, the solvent is evaporated and the remaining residue is distilled under highly reduced pressure.

17.2 g (86% of th.) D-(+)-2-/..-4-(4-bromo-2-chlorophenoxy)-phenoxy.7-propionic acid ethyl ester, b.p. 190°–193° C./0.025 mm, $\alpha_D^{20}=4.5°$ (1 m, chloroform) are obtained.

Example 10

D-(+)-2-/..-4-(4-bromo-2-chloro-phenoxy)-phenoxy.7-propionic acid-methyl ester

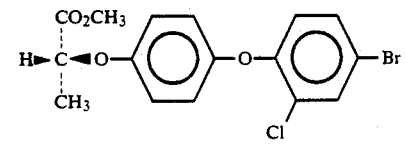

94.2 g (0.236 mol) of D-(+)-2-/-4-(4-bromo-2-chloro-phenoxy)-phenoxy.7-propionic acid ethyl ester (see Example 9) are dissolved in 700 cc of methanol. 3 cc of concentrated sulfuric acid are added and the batch is refluxed for 8 hours. The mixture obtained is substantially freed from methanol and ethanol by vacuum distillation, then 700 cc of methanol are added and the batch is again refluxed for 8 hours. Subsequently the methanol is distilled off, the residue is dissolved in chloroform, washed with water until it is free from acid, and the solvent, is removed by distillation. The remaining residue is fractionated under highly reduced pressure.

78.6 g (86% of th.) D-(+)-2-/-4-(4-bromo-2-chloro-phenoxy)-phenoxy.7-propionic acid methyl ester, b.p. 175°-177° C./0.03 mm, $\alpha_D^{20}=6.7°$ (1 m, chloroform) are obtained as main fraction.

The product solidifies on cooling, m.p. 51°-54° C. By recrystallization from methanol, the pure compound is obtained, m.p. 56° C., $\alpha_D^{20}$8.9° (1 m, chloroform).

Example 11

D-(+)-2-/-4-(4-trifluoromethylphenoxy)-phenoxy.7-propionic acid methyl ester

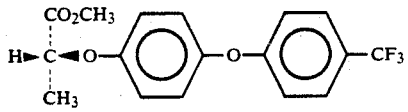

24.4 g (0.10 mol) 4-(4-trifluoromethylphenoxy)-phenol are refluxed for 15 hours together with 28.4 g (0.11 mol) of L-(−)-lactic acid methyl ester tosylate and 16.6 g (0.12 mol) of pulverized anhydrous potassium carbonate in 150 cc of acetonitrile. After cooling, the product is filtered off from the Drecipitated salt residue, the solvent is evaporated, and the remaining residue is distilled under highly reduced pressure.

30.6 g (90% of th.) D-(+)-2-/-4-(4-trifluoromethylphenoxy)-phenoxy.7-propionic acid methyl ester, b.p. 157°-159° C./0.04 mm $\alpha_D^{20}=7.0°$ (1 m, chloroform) are obtained.

Example 12

D-(+)-2-/-4-(4-trifluoromethylphenoxy)-phenoxy.7-propionic acid-ethyl ester

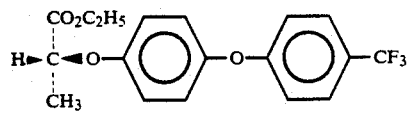

152.4 g (0.6 mol) 4-(4-trifluoromethylphenoxy)-phenol are refluxed for 72 hours together with 179.5 g (0.66 mol) of L-(−)-lactic acid ethyl ester tosylate and 015.2 g (0.69 mol) of pulverized, anhydrous potassium carbonate in 1000 cc of acetone. After cooling t-he product is filtered off from the precipitated salt residue, the solvent is evaporated, and the remaining residue is distilled under highly reduced pressure.

206 g (97% of th.) D-(+)-2-/-4-(4-trifluoromethylphenoxy)-phenoxy.7-propionic acid ethyl ester, b.p. 150°-156° C./0.05 mm, $\alpha_D^{20}=5.0°$ (1 m, chloroform) are obtained.

The product solidifies on cooling, m.p. 58°-64° C. By recrystallization from ethanol, the pure compound is obtained, m.p. 68.5° C., $\alpha_D^{20}=9.3°$ (1 m, chloroform).

Example 13

D-(+)-2-/-4-(2,4-dichlorobenzyl)-phenoxy.7-propionic acid ethyl ester

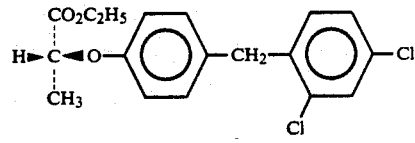

38.0 g (0.150 mol) of 4-(2,4-dichlorobenzyl)-phenol are refluxed for 22 hours together with 44.9 g (0.165 mol) of L-(−)-lactic acid-ethyl ester tosylate and 28.4 g (0.180 mol) of pulverized anhydrous potassium carbonate in 200 cc of acetonitrile. After cooling the product is filtered off from the salt, residue, the solvent is evaporated and the remaining residue distilled under highly reduced pressure. 36.7 g (69% of th.) D-(+)-2-/-4-(2,4-dichlorobenzyl)-phenoxy.7-propionic acid ethyl ester, b.p. 160° C./0.02 mm, $\alpha_D^{20}=7.0°$ (1 m, chloroform) are obtained.

Example 14

D-(+)-2-/-4-(2,4-dichlorobenzyl)-phenoxy.7-propionic acid methyl ester

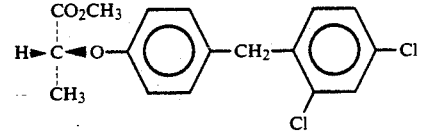

22.8 g (0.062 mol) of D-(+)-2-/-4-(2,4-dichlorobenzyl)-phenoxy.7-propionic acid ethyl ester (see Example 13) are dissolved in 1600 cc of methanol. 3 cc of concentrated sulfuric acid are added and the batch is refluxed for 30 hours. Subsequently, the methanol is distilled off, the residue is dissolved in chloroform, washed with water until it is free from acid and the solvent is removed by distillation. The remaining residue is fractionated under highly reduced pressure.

19.9 g (90% of th.) D-(+)-2-/-4-(2,4-dichlorobenzyl)-phenoxy.7-propionic acid methyl ester, b.p. 180° C./0.15 mm, $\alpha_D^{20}=7.6°$ (1 m, chloroform) are obtained.

Example 15

D-(+)-2-/-4-(5-chloro-2-benzoxazolyloxy)-phenoxy.7-propionic acid ethyl ester

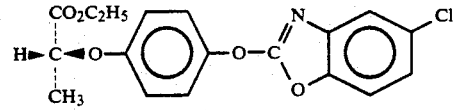

26.2 g (0.1 mol) of 4-(5-chloro-2-benzoxazolyloxy)-phenol are heated for 1 hour ½ to boiling temperature together with 16.6 g (0.12 mol) of potassium carbonate in 120 ml of acetonitrile. Subsequently, 29.9 g (0.11 mol) of L-(−)-lactic acid ethyl ester tosylate, dissolved in 50 ml acetonitrile, are added dropwise within 15 minutes.

The reaction mixture is maintained at reflux temperature for 12 hours, the salt precipitate is filtered off and acetonitrile is distilled off from the filtrate. The remaining residue is dissolved in 200 ml methylene chloride and washed twice with 200 cc each of water. After drying over sodium sulfate, methylene chloride is distilled off. The residue obtained is fractionated, yielding 29.8 g (82.5% of th.) 2-/- -4-(5-chloro-2-benzoxyzolyloxy)-phenoxy.7-proptonic acid-ethyl ester, m.p. 53°-55° C. and $\alpha_D{}^{20} = 11.3°$ (1 m, chloroform), substantially containing D-(+).

Example 16

D-(+)-2-/- -4-(6-chloro-2-benzothiazolyloxy)-phenoxy.7-propionic acid ethyl ester

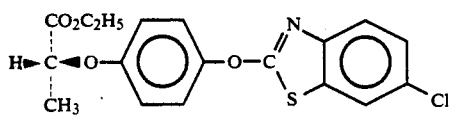

27.8 g (0.1 mol) of 4-(6-chloro-2-benzothiazolyloxy)-phenol are refluxed for 1 hour 112 together with 16.6 g (0.12 mol) of potassium carbonate in 120 cc of acetonitrile. Subsequently, 29.9 g (0.11 mol) of L-(−)-lactic acid ethyl ester tosylate, dissolved in 50 cc of acetonitrile, are added dropwise within 15 minutes. The reaction mixture is maintained at reflux temperature for 5 hours, the salt precipitate is then filtered off and acetonitrile is distilled off from the filtrate. The remaining residue is dissolved in 200 cc of methylene chloride, washed twice with 100 cc each of water, and after drying over sodium sulfate the methylene chloride is distilled off. The remaining residue due is fractionated, yielding 34.5 g (91.4% of th.) 2-/- -4-(6-chloro-2-benzothiazolyloxy)-phenoxy.7-propionic acid ethyl ester, m.p. 49° C. and $\alpha_D{}^{20} = 9.5°$ (1 m, chloroform), substantially containing D-(+). After recrystallization from an ethanol/water mixture, the product becomes optically purer, and has then a m.p. of 51°, and an $\alpha_D{}^{20} = 11°$ (1 m, chloroform).

Example 17

D-(+)-2-/- -4-(3,5-dichloro-2-pyridyloxy)-phenoxy.7-propionic acid-ethyl ester

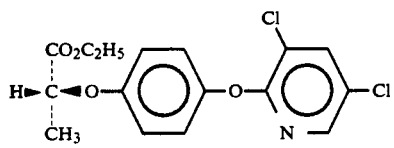

19.7 g (0.077 mol) of 4-(3,5-dichloro-2-pyridyloxy)-phenol are heated to reflux temperature with 12.7 g (0.092 mol) of potassium carbonate (anhydrous) in 150 cc of acetonitrile. Subsequently, 23 g (0.085 mol) of L-(−)-lactic acid ethyl ester tosylate, dissolved in 50 cc of acetonitrile, are added dropwise within 5 minutes. The reaction mixture is kept at reflux for 18 hours. After cooling the salt precipitate is suction-filtered and acetonitrile is distilled off from the filtrate. The oily residue is dissolved in 200 cc of toluene and washed twice with 100 cc each of water. After drying over sodium sulfate the toluene is distilled off and the remaining residue is distilled. 24.8 g (90.4% of th.) of D-(+)-2-/-4-(3,5 -dichloro-2-pyridyloxy)-phenoxy.7-propionic acid ethyl ester, b.p.$_{0.01}$:174°-176° C. and $\alpha_D{}^{20} = 9.7°$ (1 m, chloroform) are obtained.

Example 18

D-(+)-N,N-di-n-propylammonium-2/- -4-(4-chlorophenoxy) -phenoxy.7-propionate

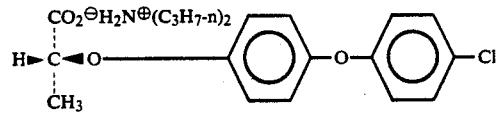

13.2 g (45 mmols) of the acid of Example 4 are dissolved in toluene with warming. At about 30° C., 4.5 g (45 mmols) of di-n-propylamine are added with stirring. Stirring is continued for a short, time, then the precipitate is suction-filtered. After drying 17.0 g of the salt are obtained having a m.p. of 125°-125.5° C., /.-α.7$_{20}$+20.4° (chloroform).

Example 19

D-(−)-sodium-2-/- -4-(2-chloro-4-trifluoromethyl-phenoxy) -phenoxy.7-propionate

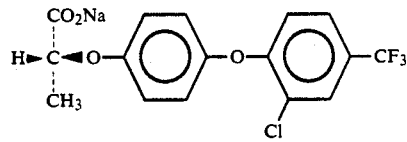

16.2 g (45 mmols) of the acid of Example 5 are dissolved in ethanol with warming. A solution of 1.8 g (45 mmols) sodium hydroxide in water is added. The solvents are then evaporated, finally under reduced pressure. 17.1 g of the sodium salt having a m.p. of 78°-81° C., /.-α.7$_D$−18.9° are obtained.

Example 20

(D+)-ethyl-2/- -4-(6-chloro-2-benzoxazolyloxy)-phenoxy.7-propionate 31.5 g (0.15 mol) of (D+)-ethyl-2-(4-hydroxyphenoxy) -propionate /.-α.7 $_D{}^{20}$ − 37.4° (1 n CHCL₃) are heated to reflux temperature for 1 hour with 24.9 g (0.18 mol) of potassium carbonate in 200 cc of acetonitrile. Subsequently, 28.2 g (0.15 mol) of 2,6-dichlorobenzoxazole in 80 cc of acetonitrile are added dropwise within 45 minutes. After 1 hour a further 0.85 g of 2,6-dichlorobenzoxazole are added. ½ hour after this addition, thin-layer chromatography indicates complete reaction. The reaction mixture is cooled and filtered at 30° C. in order to remove the precipitated salt, the filtrate is then concentrated and dried at 80° C. under reduced pressure. 54.2 g of an ocher-colored solid are obtained which is subsequently recrystallized twice from hexane with addition of animal charcoal. 37.4 g (D+)-ethyl-2-/- -4-(6-chloro-2-benzoxazolyloxy)-phenoxy.7-propionate, m.p. 78.5° C., angle of rotation: /.-α.7$_D{}^{25}$: 30° (1 n CHCL₃) are obtained.

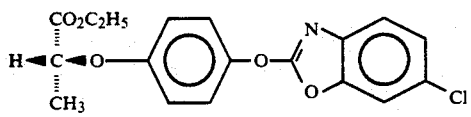

Example 21

D-(+)-2-/_-
-4-(2-nitro-4-trifluoromethyl)-phenoxy_7-propionic acid ethyl ester

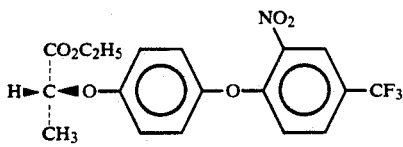

11.3 g (50 mmols) of 3-nitro-4-chlorobenzotrifluoride are refluxed for 7.5 hours together with 10.5 g (50 mmols) of D-2(4-hydroxy-phenoxy)propionic acid ethyl ester and 8.3 g (60 mmols) of dry, pulverized potassium carbonate in 100 cc of acetonitrile. The product is filtered off from the salt mixture and the solvent is removed under reduced pressure. 20.3 g of D-(+)-2-/_-
-4-(2-nitro-4-trifluoromethyl-phenoxy) -phenoxy_7-propionic acid methyl ester are obtained, which can be recrystallized from ethanol for further purification. The recrystallized product has a melting point of 85°-87° C., /_-α_7_D_ = +21.7°.

Example 22

D-(−)-2/_-
-4-(2,4-Dichlorophenoxy)-phenoxy_7-n-propanol

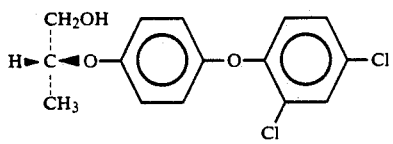

A solution of 35.5 g (0.10 mol) of D-(+)-2-/_-
-4-(2,4-dichlorophenoxy)-phenoxy 7-propionic acid ethyl ester (see Example 20) in 40 cc of tetrahydrofuran is added dropwise within 1 hour to a refluxed suspension of 5.7 g (0.15 mol) lithium aluminum hydride in 70 cc of tetrahydrofuran. After refluxing for another 1 ½ hours the batch is cooled, then 20 cc of ethyl acetate are added slowly, and subsequently 100 cc of dilute sulfuric acid. The organic phase is separated, the aqueous phase is extracted twice with 50 cc each of tetrahydrofuran, and the united tetrahydrofuran phases are concentrated. The residue is dissolved in chloroform, the solution is washed with water and dried. On evaporation of the solvent-, 30.0 g of crude D-(−)-2-/_-
-4-(2,4-dichlorophenoxy)-phenoxy_7-n-propanol are obtained. The product can be purified by column chromatography. $n_D^{20}$1.5795, /_-α_7_D_ −18.3°.

Example 23

D-(−)-2-/_-
-4-(2,4-dichlorophenoxy)-phenoxy_7-propionic acid-N,N-diethylamide

A solution of 15.5 g (45 mmols) of D-2-/_-
-4-(2,4-dichlorophenoxy)-phenoxy_7-propionic acid chloride (see Example 21) is added dropwise within 1 hour to a solution of 7.2 g (99 mmols) of diethylamide in 20 cc of toluene. The product is suction-filtered from the amine/hydrochloride precipitate which has formed, the filtrate is washed with dilute hydrochloric acid and water. After drying and evaporation of the solvent, 15.1 g of oily D-(−)-2-/_-4-(2,4-dichlorophenoxy)-phenoxy_7-propionic acid-N,N-diethylamide, $n_D^{20}$ 1.5652, /_-α_7_D_ −1.7° are obtained.

Example 24

D-2-/_-
-4-(2,4-dichlorophenoxy)-phenoxy_7-propionitrile

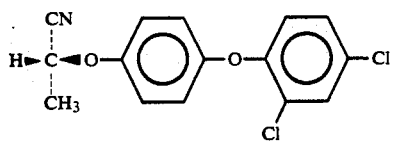

14.8 g (45 mmols) of D-2-/_-4-(2,4-dichlorophenoxy) -phenoxy_7-proptonamide (Example 61) are dissolved in 50 ml of toluene and 50 ml (0.68 mol) of thionyl chloride are added. The batch is refluxed for 16 ½ hours, subsequently toluene and unreacted thionyl chloride are distilled off, finally under reduced pressure. The dark residue is dissolved in chloroform, washed with sodium bicarbonate solution and water and dried. After evaporation, 14.9 g of crude D-2-/_-
-4-(2,4-dichlorophenoxy)-phenoxy_7-propionitrile are obtained which can be further purified by column chromatography, yielding 10.2 g (73% of th.) product having a refractive index $n_D^{20}$ of 1.5710.

Example 25

D-(−)-2-/_-
-4-(2,4-dichlorophenoxy)-phenoxy_7-propionic acid thioamide

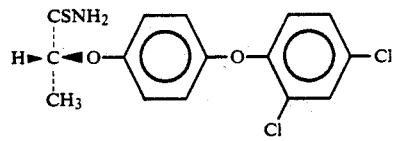

13.0 g (40 mmols) of D-2-/_-4-(2,4-dichlorophenoxy) -phenoxy_7-propionamide (Example 61) in 150 cc of acetonitrile are stirred for 23 hours at room temperature together with 5.1 g (50 mmols) of triethylamine and 17.8 g (40 mmols) of $P_4S_{10}$. The product is then filtered off from the precipitated solids, the solvent is evaporated under reduced pressure and the remaining residue is dissolved in chloroform. Undissolved residues are removed. The chloroform phase is then washed with dilute hydrochloric acid, sodium hydroxide solution and water, dried and evaporated. 10.3 g (75% of th.) of crude D-(−)-2-/_-
-4-(2,4-dichlorophenoxy)-phenoxy_7-propionic acid thioamide are obtained. After recrystallization from ethanol, light yellow crystals are obtained, m.p. 153°-153.5° C., /_-α_7_D_ −15.4°.

In analogous manner, there are obtained:

| Example No. | Structure | physical data | prepared according to Ex. |
|---|---|---|---|
| 26 | (S)-CH(CO$_2$C$_2$H$_5$)(CH$_3$)-O-C$_6$H$_4$-O-C$_6$H$_3$(Cl)(CF$_3$) | $[\alpha]_D$ + 18.9° | 1 |
| 27 | (S)-CH(CO$_2$C$_2$H$_5$)(CH$_3$)-O-C$_6$H$_4$-CH$_2$-C$_6$H$_4$-Cl (in mixture with 40% (S)-CH(CO$_2$C$_2$H$_5$)(CH$_3$)-O-C$_6$H$_4$-CH$_2$-C$_6$H$_4$-Cl (ortho isomer) ) | $n_D^{20}$ 1.5481 $[\alpha]_D$ + 23.7° | 1 |
| 28 | (S)-CH(COOH)(CH$_3$)-O-C$_6$H$_4$-O-C$_6$H$_3$(Cl)(CF$_3$) | m.p. 84–88° C. $[\alpha]_D$ + 12.1° | 2 |
| 29 | (S)-CH(COOH)(CH$_3$)-O-C$_6$H$_4$-O-C$_6$H$_3$(Cl)$_2$ | m.p. 78–80° C. $[\alpha]_D$ + 12.6° | 2 |
| 30 | (S)-CH(COOH)(CH$_3$)-O-C$_6$H$_4$-CH$_2$-C$_6$H$_4$-Cl (in mixture with 40% (S)-CH(COOH)(CH$_3$)-O-C$_6$H$_4$-CH$_2$-C$_6$H$_4$-Cl (ortho isomer) ) | $[\alpha]_D$ + 11.0° | 2 |
| 31 | (S)-CH(COOH)(CH$_3$)-O-C$_6$H$_4$-CH$_2$-C$_6$H$_3$(Cl)$_2$ | m.p. 69–78° C. $[\alpha]_D$ + 11.1° | |
| 32 | (S)-CH(COONa)(CH$_3$)-O-C$_6$H$_4$-O-C$_6$H$_3$(Cl)$_2$ | m.p. 80° C. $[\alpha]_D$ + 18.3° | 19 |

-continued

| Example No. | Structure | physical data | prepared according to Ex. |
|---|---|---|---|
| 33 | COOK–CH(CH$_3$)–O–C$_6$H$_4$–O–C$_6$H$_3$(Cl)–Br | $[\alpha]_D$ − 11.0° | 19 |
| 34 | COO$^\ominus$ NH$_4^\oplus$–CH(CH$_3$)–O–C$_6$H$_4$–O–C$_6$H$_4$–CF$_3$ | $[\alpha]_D$ + 6.9° | 19 |
| 35 | CO$_2^\ominus$ H$_2$N$^\oplus$(CH$_3$)$_2$–CH(CH$_3$)–O–C$_6$H$_4$–O–C$_6$H$_3$(Cl)–Cl | m.p. 67–68° C. $[\alpha]_D$ + 22.1° | 18 |
| 36 | CO$_2^\ominus$ H$_2$N$^\oplus$(CH$_3$)$_2$–CH(CH$_3$)–O–C$_6$H$_4$–O–C$_6$H$_3$(Cl)–Br | m.p. 65–75° C. $[\alpha]_D$ + 11.9° | 18 |
| 37 | COO$^\ominus$ H$_3$N$^\oplus$CH$_3$–CH(CH$_3$)–O–C$_6$H$_4$–O–C$_6$H$_4$–CF$_3$ | $[\alpha]_D$ + 10.2° | 19 |
| 38 | COONa–CH(CH$_3$)–O–C$_6$H$_4$–CH$_2$–C$_6$H$_3$(Cl)–Cl | m.p. 95–96° C. $[\alpha]_D$ + 4.6° | 19 |
| 39 | CO$_2$CH(CH$_3$)$_2$–CH(CH$_3$)–O–C$_6$H$_4$–O–C$_6$H$_3$(Cl)–CF$_3$ | $n_D^{20}$ 1.5085 | 6 |
| 40 | CO$_2$CH$_2$–CH(CH$_3$)(H)–O–C$_6$H$_4$–O–C$_6$H$_3$(Cl)–Cl ; CH(CH$_3$)–O–C$_6$H$_4$–O–C$_6$H$_3$(Cl)–Cl | $n_D^{20}$ 1.5796 $[\alpha]_D$ − 6.1° | 6 |

Remark: (Preparation of the alcohol component see Ex. 22)

-continued

| Example No. | Structure | physical data | prepared according to Ex. |
|---|---|---|---|
| 41 | 2,4-Cl$_2$-C$_6$H$_3$-O-CH$_2$-C(H)(CH$_3$)-; H-C(CH$_3$)-O-C$_6$H$_4$-O-C$_6$H$_3$(2,4-Cl$_2$) with CO$_2$CH$_2$ linker | $n_D^{20}$ 1.5750<br>$[\alpha]_D$ − 9.0° | 6 |
| 42 | CO$_2$C$_5$H$_{11}$(n); H-C(CH$_3$)-O-C$_6$H$_4$-O-C$_6$H$_3$(2,4-Cl$_2$) | $n_D^{20}$ 1.5437<br>$[\alpha]_D$ + 13.5° | 6 |
| 43 | CO$_2$CH$_2$-C$_6$H$_3$(3,4-Cl$_2$); H-C(CH$_3$)-O-C$_6$H$_4$-O-C$_6$H$_3$(2,4-Cl$_2$) | $n_D^{20}$ 1.5900<br>$[\alpha]_D$ + 8.9° | 6 |
| 44 | CO$_2$CH$_2$-C≡CH; H-C(CH$_3$)-O-C$_6$H$_4$-O-C$_6$H$_4$-Cl | $n_D^{20}$ 1.5605<br>$[\alpha]_D$ + 16.4° C. | 6 |
| 45 | CO$_2$CH$_3$; H-C(CH$_3$)-O-C$_6$H$_4$-O-C$_6$H$_4$-Cl | $n_D^{20}$ 1.5588<br>$[\alpha]_D$ + 21.5° | 6 |
| 46 | CO$_2$C$_8$H$_{17}$(n); H-C(CH$_3$)-O-C$_6$H$_4$-O-C$_6$H$_4$-Cl | $n_D^{20}$ 1.5240<br>$[\alpha]_D$ + 11.5° | 6 |
| 47 | CO$_2$CH$_2$CH$_2$CH(CH$_3$)$_2$; H-C(CH$_3$)-O-C$_6$H$_4$-O-C$_6$H$_4$-Cl | $n_D^{20}$ 1.5349<br>$[\alpha]_D$ + 16.3° | 6 |
| 48 | CO$_2$CH$_2$CH$_2$Cl; H-C(CH$_3$)-O-C$_6$H$_4$-O-C$_6$H$_4$-Cl | m.p. 52°<br>$[\alpha]_D$ + 12.4° | 6 |

-continued

| Example No. | Structure | physical data | prepared according to Ex. |
|---|---|---|---|
| 49 | CH₃-C(H)(CO₂C₃H₇(n))-O-C₆H₄-O-C₆H₃(Cl)-Br | $n_D^{20}$ 1.5780 | 6 |
| 50 | CH₃-C(H)(CO-SCH₂-C₆H₄-Cl)-O-C₆H₄-O-C₆H₃(Cl)-Br | $n_D^{20}$ 1.6180 | 6 |
| 51 | CH₃-C(H)(CO₂CH(CH₃)CH₂CH₃)-O-C₆H₄-O-C₆H₃(Cl)-Br | $n_D^{20}$ 1.5860 | 6 |
| 52 | CH₃-C(H)(CO₂CH₂CH₂SCH₂CH₃)-O-C₆H₄-O-C₆H₃(Cl)-Br | $n_D^{20}$ 1.5880 | 6 |
| 53 | CH₃-C(H)(CO₂CH₂CH(CH₃)₂)-O-C₆H₄-O-C₆H₄-CF₃ | | 6 |
| 54 | CH₃-C(H)(CO₂CH₂CH=CH₂)-O-C₆H₄-O-C₆H₄-CF₃ | m.p. 48–54° C. | 6 |
| 55 | CH₃-C(H)(CO₂CH₂CH₂-C₆H₅)-O-C₆H₄-O-C₆H₄-CF₃ | $n_D^{20}$ 1.5324 $[\alpha]_D$ + 6.6° | 6 |
| 56 | CH₃-C(H)(CO₂CH₂CH(CH₃)₂)-O-C₆H₄-CH₂-C₆H₄-Cl | $n_D^{20}$ 1.5411 $[\alpha]_D$ + 4.1° | 6 |

-continued

| Example No. | Structure | physical data | prepared according to Ex. |
|---|---|---|---|
| | (mixture with 40% [structure: CO2CH2CH(CH3)2, H-C-O-phenyl-CH2-phenyl-Cl, CH3]) | | |
| 57 | [structure: CO2-cyclohexyl-Cl, H-C-O-phenyl-CH2-phenyl-Cl, CH3] and [structure: CO2-cyclohexyl-Cl, H-C-O-phenyl(CH2-phenyl-Cl), CH3] | $n_D^{20}$ 1.5550 $[\alpha]_D$ − 10.4° | 6 |
| 58 | [structure: CO2-cyclopentyl, H-C-O-phenyl-CH2-(2,4-dichlorophenyl), CH3] | $n_D^{20}$ 1.5636 $[\alpha]_D$ − 11.9° | 6 |
| 59 | [structure: CO-SCH2-phenyl, H-C-O-phenyl-CH2-(2,4-dichlorophenyl), CH3] | $n_D^{20}$ 1.6042 $[\alpha]_D$ + 15.4° | 6 |
| 60 | [structure: CO2CH2-C(Cl)=CH2, H-C-O-phenyl-O-(2-chloro-4-bromophenyl), CH3] | | |

-continued

| Example No. | Structure | physical data | prepared according to Ex. |
|---|---|---|---|
| 61 | CONHNHCH₃ group, H–C(CH₃)–O–C₆H₄–O–C₆H₃(Cl)(Cl) | $n_D^{20}$ 1.5850<br>$[\alpha]_D$ − 21.1° | 23 |
| 62 | CONH₂ group, H–C(CH₃)–O–C₆H₄–O–C₆H₃(Cl)(Cl) | m.p. 130–131° C.<br>$[\alpha]_D$ − 16.0° | 23 |
| 63 | CON(CH₃)₂ group, H–C(CH₃)–O–C₆H₄–O–C₆H₄–Cl | $n_D^{20}$ 1.5742<br>$[\alpha]_D$ − 10.1° | 23 |
| 64 | CONHNH–C₆H₅, H–C(CH₃)–O–C₆H₄–O–C₆H₃(Cl)(Br) | m.p. 150–151° C.<br>$[\alpha]_D$ − 25.0° | 23 |
| 65 | CONH–C₆H₄–Cl, H–C(CH₃)–O–C₆H₄–O–C₆H₄–CF₃ | m.p. 119–120° C. | 23 |
| 66 | CONH–CH(CH₃)–C₆H₅, H–C(CH₃)–O–C₆H₄–O–C₆H₄–CF₃ | m.p. 94–99° C.<br>$[\alpha]_D$ 21.6° | 23 |
| 67 | CON(CH₃)(C₄H₉(n)), H–C(CH₃)–O–C₆H₄–CH₂–C₆H₄–Cl | $n_D^{20}$ 1.5549<br>$[\alpha]_D$ − 16.8° | 23 |

| Example No. | Structure | physical data | prepared according to Ex. |
|---|---|---|---|
| | (mixture with 40% [structure: CON(CH₃)(C₄H₉(n)), H►C◄O-phenyl-CH₂-phenyl-Cl, CH₃]) | | |
| 68 | [structure: CONH-cyclohexyl-H, H►C◄O-phenyl-CH₂-(2,4-dichlorophenyl), CH₃] | m.p. 94–106° $[\alpha]_D - 22.3°$ | 23 |
| 69 | [structure: CON(CH₃)(OCH₃), H►C◄O-phenyl-CH₂-(2,4-dichlorophenyl), CH₃] | $n_D^{20}$ 1.5703 $[\alpha]_D - 5.7°$ | 23 |

BIOLOGICAL EXAMPLES

The optically active D-(+) compounds (for details, see Tables), compared with the corresponding racemates, were tested against diverse weed grasses in open air trials in post emergence application. The size of the plots was 5 and 10 m², respectively; the tests were repeated 3 to 4 times. The compounds were formulated as emulsions concentrates, and applied in varying concentration per ha relative to an amount, of 500 l water/ha, that is, the amount of liquid per ha was 500 l in each case.

30 to 35 days after treatment the effect of the products was determined according to the BBA scheme 1-9 (of Biologische Bundesanstalt, Braunschweig, West-Germany), see following Table:

| rating No. | damage in % to | |
|---|---|---|
| | weeds | crop plants |
| 1 | 100 | 0 |
| 2 | 97.5 to <100 | 0 to >2.5 |
| 3 | 95 to <97.5 | 2.5 to >5 |
| 4 | 90 to <95 | 5 to >10 |
| 5 | 85 to <90 | 10 to >15 |
| 6 | 75 to <85 | 15 to >25 |
| 7 | 65 to <75 | 25 to >35 |
| 8 | 32.5 to <65 | 35 to >67.5 |
| 9 | 0 to <32.5 | 67.5 to >100 |

Furthermore, the tolerability of the products to crop plants was tested for the first time one week after the treatment.

The $ED_{95}$ and $ED_{98}$ values listed in the Tables indicate at what dose/ha of active substance 95 and 98% of the weed plants were destroyed (ED=effective dose).

Example I

Treatment of annual blackgrass (*Alopecurus myosuroides*) in sugar beets according to the post emergence process.

At the time of treatment the sugar beets were in the 6 to 8 leaves stage. The ED values are indicated in Table I.

TABLE I

| | Compound of Example (3) kg/ha AS | Racemate kg/ha AS | Relation optically:racemate active compound |
|---|---|---|---|
| $ED_{95}$ | 0.44 | 0.76 | 1:1.73 |
| $ED_{98}$ | 0.66 | 1.10 | 1:1.67 |

As compared to the racemate, the savings of active substance were therefore 43 and 40%, respectively. No phytotoxis was observed on the treated sugar beets.

Example II

Activity against barnyard grass (*Echinochloa crusgalli*) in sugar beets (stage of 4 to 6 leaves) in post-emergence application (results see Table II).

TABLE II

|  | Compound of Example (3) kg/ha AS | Racemate kg/ha AS | Relation compound:racemate |
|---|---|---|---|
| ED95 | 0.16 | 0.27 | 1:1.68 |
| ED98 | 0.34 | 0.55 | 1:1.62 |

As compared to the racemate, the savings of the active substance, at an equal success of treatment, were 38 and 41%, respectively. The sugar beets were not damaged.

Example III

Activity against wild oat (*Avena fatua*) and annual blackgrass (*Alopecurus myosuroides*) in sugar beets (stage of 6 leaves) in post-emergence application (results see Table III).

TABLE III

|  | Compound of Example (10) kg/ha AS | Racemate kg/ha AS | Relation compound:racemate |
|---|---|---|---|
| ED95 Avena f. | 0.44 | 0.80 | 1:1.82 |
| ED98 Alopecurus | 0.52 | 0.95 | 1:1.83 |

As compared to the racemate, the savings of active substance, at equal success of treatment, were thus 45%. No phytotoxis was observed on the crop plants.

Example IV

Activity against wild oat and annual blackgrass in sugar beets (6-leaf stage) in post-emergence appl. (results see Table IV).

TABLE IV

|  | Compound of Example (3) kg/ha AS | Racemate kg/ha AS | Relation compound:racemate |
|---|---|---|---|
| Alopecurus |  |  |  |
| ED95 | 0.15 | 0.32 | 1:2.14 |
| ED98 | 0.25 | 0.42 | 1:1.68 |
| Avena f. |  |  |  |
| ED95 | 0.21 | 0.55 | 1:2.62 |
| ED98 | 0.25 | 0.65 | 1:2.60 |

Thus, as compared to the racemate, the savings of active substance when combating annual blackgrass were 53 and 41%, respectively. The savings in the case of wild oat were 62%.

When the ethyl ester of Example (1) is used under the same conditions, the savings of active substance were about 42%.

Example V

|  | Racemate kg/ha AS | relatively | compound of Example (4) kg/ha AS | relatively |
|---|---|---|---|---|
| ED98 | 1.10 | 100 | 0.65 | 59 |

Thus, as compared to the racemate, an equal success of treatment was achieved with 41% of optically active material only. There was no damage of the spring wheat.

What is claimed is:

1. A method for combating undesirable plant growth which comprises applying thereto a herbicidally effective amount of an optically active compound which is ethyl-2-(4-(6-chloro-benzoxazol-2-yloxy)-phenoxy)-propionate containing at least 80% of the D-form of formula

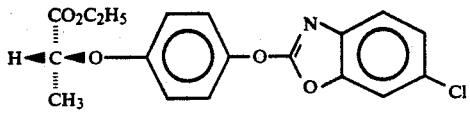

and containing less than 20 percent of the L-form.

2. A method as claimed in claim 1, wherein the optically active compound contains less than 10% by weight of the L-form.

3. A method as claimed in claim 1, wherein the optically active compound contains less than 5% by weight of the L-form.

4. A method as claimed in claim 1, wherein said compound is applied at a rate of from 0.05 to 3 kg/ha.

5. A method as claimed in claim 1, wherein said compound is applied at a rate of from 0.05 to 2.4 kg/ha.

6. A method as claimed in claim 1, wherein the weed plant to be combated is *Echinochloa crus-galli, Alopecurus myosuroides* or *Avena fatua*.

7. Optically active ethyl-2-(4-(6-chloro-benzoxazol-2-yloxy)-phenoxy) -propionate containing at least 80% of the D-form of formula

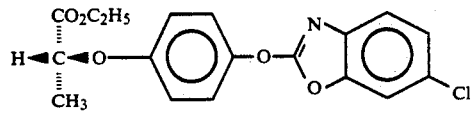

and containing less than 20 percent of the L-form.

8. Optically active ethyl-2-(4-(6-chloro-benzoxazol-2-yloxy)-phenoxy)-propionate as claimed in claim 7, which contains less than 10% by weight of the L-form.

9. Optically active ethyl-2-(4-(6-chloro-benzoxazol-2-yloxy)-phenoxy)-propionate as claimed in claim 7, which contains less than 5% by weight of the L-form.

10. A herbicidal agent comprising 2 to 95% by weight of optically active ethyl-2-(4-(6-chloro-benzoxazol-2-yloxy)-phenoxy)-propionate as claimed in claim 7, and 98 to 5% by weight of common formulation auxiliaries.

11. A method for combating undesirable plant growth which comprises applying thereto a herbicidally effective amount of substantially 100% D-form, D-enantiomer of the formula:

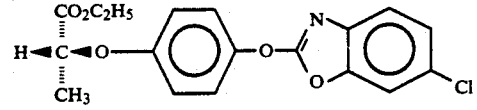

12. A herbicidal agent containing substantially 100% D-form, D-enantiomer of an optically active compound of formula:

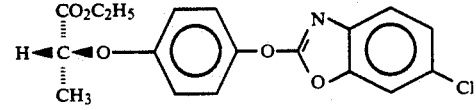

and a suitable carrier therefor.

* * * * *